US00RE35814E

United States Patent [19]

Olson

[11] E Patent Number: Re. 35,814

[45] Reissued Date of Patent: Jun. 2, 1998

[54] CLEAN UP WITH CUT RESISTANT LAYER

[76] Inventor: Mary Lou Olson, 1147 Ivyhill Dr., Mendota Heights, Minn. 55118

[21] Appl. No.: 631,082

[22] Filed: Apr. 12, 1996

Related U.S. Patent Documents

Reissue of:

[64] Patent No.: 5,301,806
Issued: Apr. 12, 1994
Appl. No.: 973,467
Filed: Nov. 6, 1992

[51] Int. Cl.[6] ..... B65D 85/18; A47L 13/18

[52] U.S. Cl. ..... 206/278; 2/159; 2/160; 15/227; 206/438; 294/1.3

[58] Field of Search ..... 206/278, 438, 206/366, 365, 204; 2/159, 160; 15/104.94, 227; 294/1.3

[56] References Cited

U.S. PATENT DOCUMENTS

| | | | |
|---|---|---|---|
| 3,870,150 | 3/1975 | Hummel | 206/438 |
| 3,948,436 | 4/1976 | Bambara | 206/523 X |
| 4,347,931 | 9/1982 | Ginger et al. | 206/438 |
| 4,645,251 | 2/1987 | Jacobs | 294/1.3 |
| 4,677,697 | 7/1987 | Hayes | 2/159 |
| 4,741,565 | 5/1988 | Bagg | 294/1.3 |
| 4,758,229 | 7/1988 | Doerscher | 206/365 X |
| 4,768,818 | 9/1988 | Kolic | 294/1.3 |
| 4,788,733 | 12/1988 | Lerner | 15/104.94 |
| 4,844,293 | 7/1989 | McLaughlin | 206/278 X |
| 4,845,781 | 7/1989 | Strickland | 294/1.3 X |
| 4,902,283 | 2/1990 | Rojko et al. | 15/227 X |
| 4,951,815 | 8/1990 | Ulbrich | 206/438 X |
| 4,964,188 | 10/1990 | Olson | 15/227 |
| 5,065,863 | 11/1991 | Moget-Ortiz | 206/278 X |

*Primary Examiner*—Bryon P. Gehman

[57] ABSTRACT

The invention relates to a clean up bag, more particularly to a plastic bag that has a plastic glove which is heat sealed to one interior side of the bag. The glove has two thumbs so that it may be used by either left handed or right handed individuals. The bag is covered with a cut-resistant fabric such as Kevlar, and has a padding of fibrous material on the outside of the bag which absorbs any liquid surrounding or contained in the waste to be picked up. The bag also has a draw string closure on the top which pulls from either side. The bag is turned inside out once the waste has been cleaned up, and the draw strings used to close the bag for disposal.

18 Claims, 3 Drawing Sheets

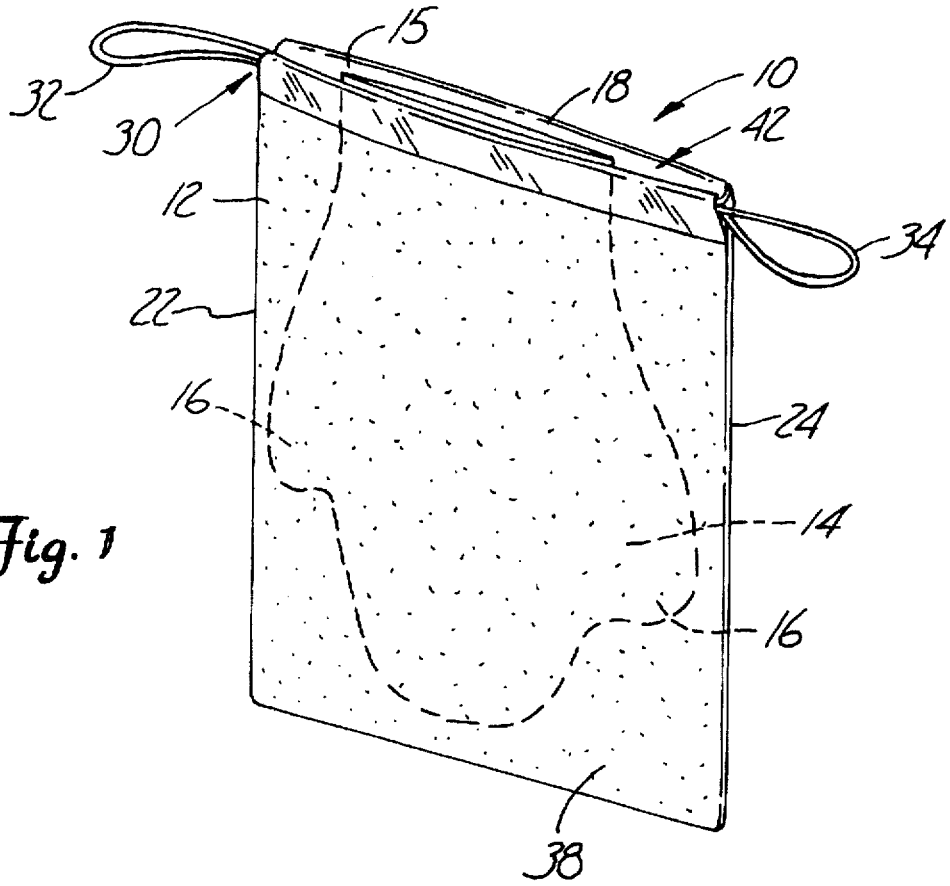
Fig. 1
Fig. 2
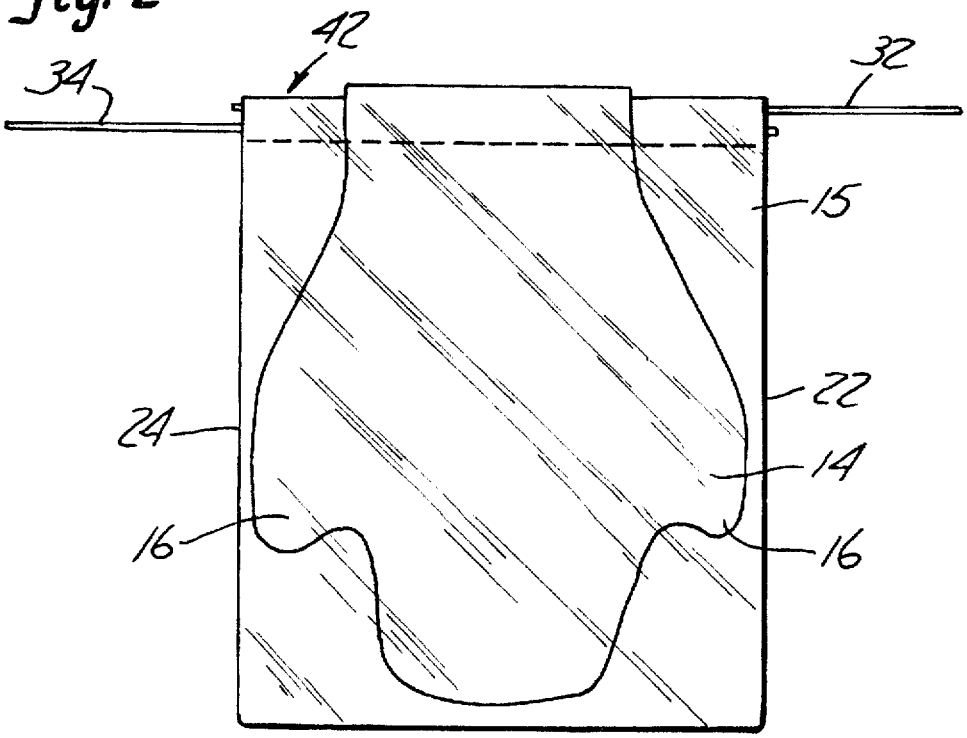

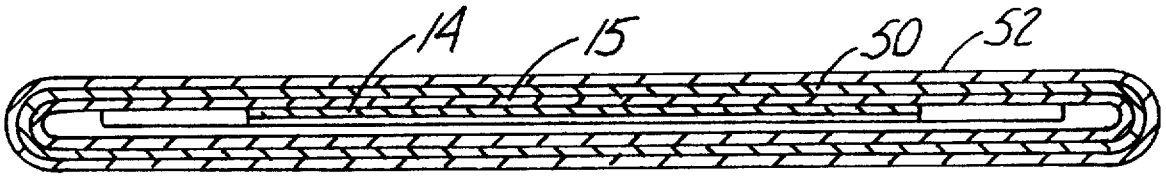
Fig. 3
Fig. 4
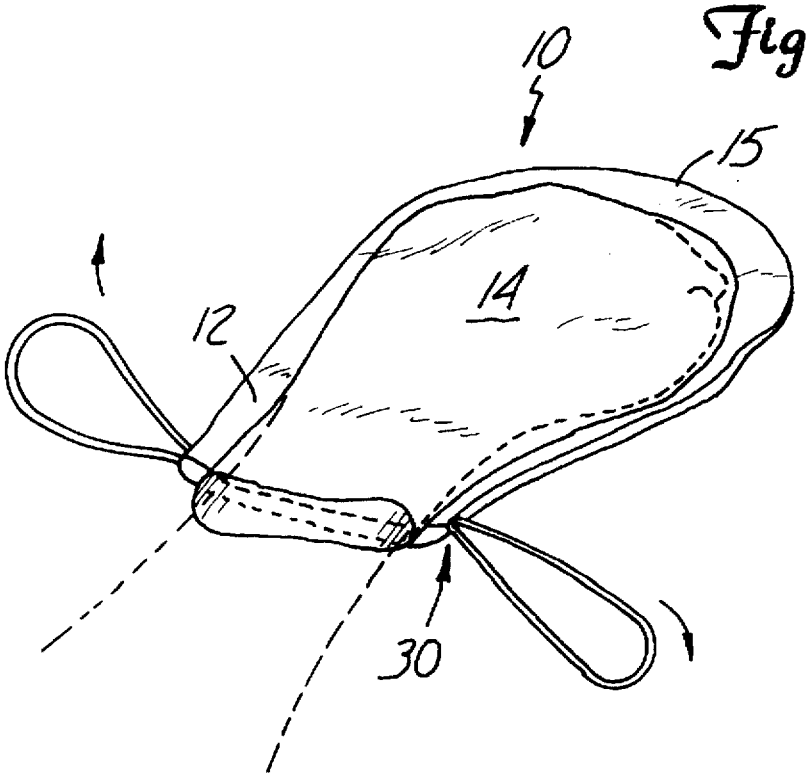

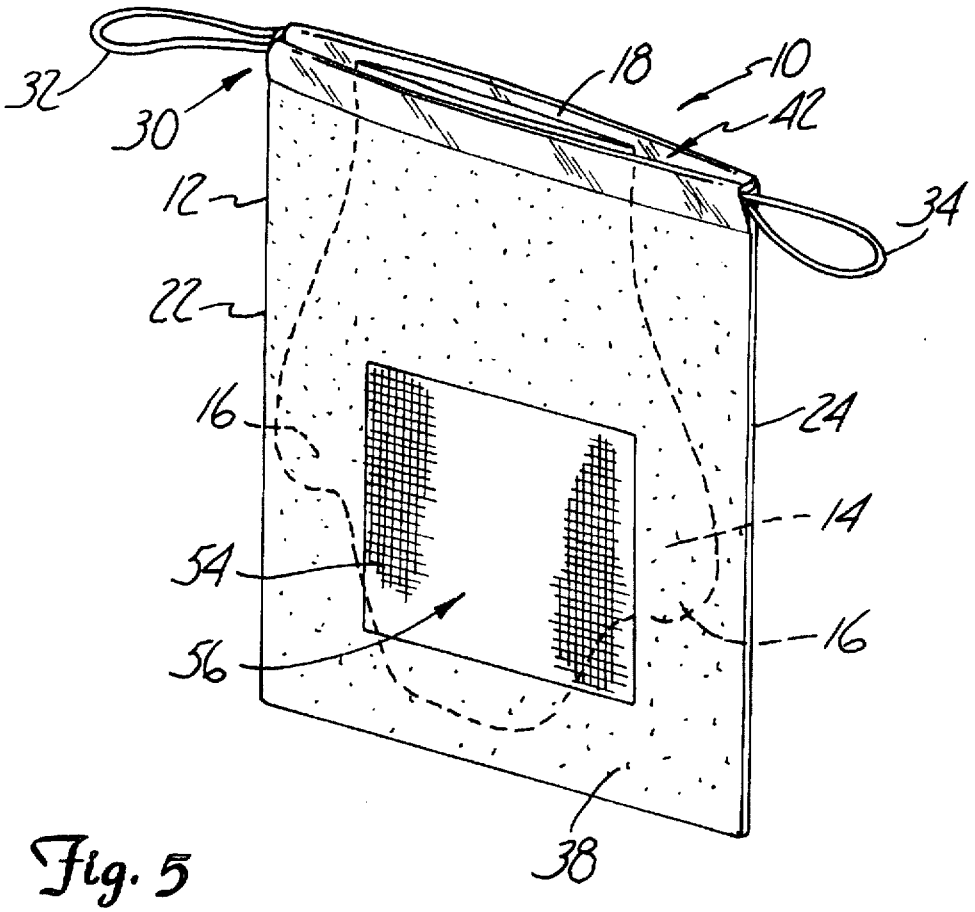
Fig. 5
Fig. 6
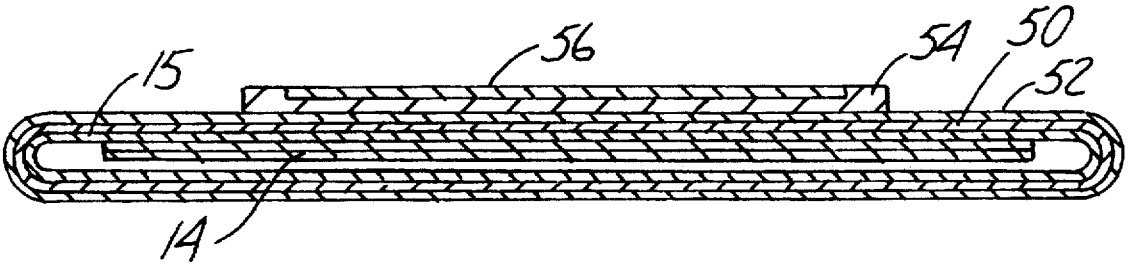

CLEAN UP WITH CUT RESISTANT LAYER

Matter enclosed in heavy brackets [ ] appears in the original patent but forms no part of this reissue specification; matter printed in italics indicates the additions made by reissue.

TECHNICAL FIELD OF THE INVENTION

This invention relates to clean up devices and methods, and more particularly to a device and method for cleaning up hazardous, infectious or toxic wastes.

BACKGROUND OF THE INVENTION

U.S. Pat. No. 4,964,188 to Olson, entitled "Clean Up Device", (the entire disclosure of which is hereby incorporated herein by reference) discloses a clean up device which includes a glove which is heat-sealed to the inside of a plastic bag. The plastic bag is used to pick up waste, and in particular animal excrement. This glove allows easy manipulation of the bag so that the excrement may be easily picked up. The glove prevents the bag from slipping around on the hand. Further, the outside of the bag has padded material mounted to the surface of the bag. This padding material helps absorb any moisture contained in the excrement so that the excrement does not slip around when the user is picking it up. Further, the padding serves as an insulator so that the user does not feel the texture or heat of the excrement.

The present invention is a further development of the device disclosed in the Olson '188 patent. The invention is particularly adapted for the clean up and disposal of hazardous, infectious and toxic wastes.

SUMMARY OF THE INVENTION

The invention relates to a clean up device, more particularly to a plastic bag that has a plastic glove which is heat-sealed to one interior side of the bag. The plastic bag is surrounded by a layer of cut-resistant material such as Kevlar™. There is an absorbent towel attached to the outside of the cut-resistant layer which absorbs any liquid surrounding or contained in the waste to be picked up. The bag also has a draw string closure on the top which pulls from either side. Optionally, the bag is opaque so that the user cannot see the contents.

According to another embodiment of the invention, a gauze pad or other such absorbent pad is attached to one side of the bag on top of the absorbent towel layer, to provide additional absorbency. This pad, or the absorbent towel layer, may be impregnated or soaked or covered with a disinfectant, in case of a medical application of the bag, or a cleaning material such as a solvent, in the case of use of the bag to clean up a toxic waste. Also, the pad may be adapted for special functions, such as for scrubbing a surface.

In operation, the user places his or her hand inside the plastic glove which is inside the bag and grasps the waste, or wipes up the waste. The padding absorbs the moisture or waste, while the cut-resistant material protects against needles or broken glass or the like from puncturing through the plastic and into the users hand. The user then turns the bag inside out so that the waste is contained inside the bag. Finally, the draw strings are pulled tight so that the bag is closed. The user may carry the waste, which is neatly contained within the bag, or the user may dispose of the bag containing the waste at the first convenient location.

BRIEF DESCRIPTION OF THE DRAWINGS

FIG. 1 is a schematic view of the clean up bag constructed in accordance with the present invention.

FIG. 2 is a schematic view of the clean up bag after being turned inside out.

FIG. 3 is a top cross-sectional view of the clean up bag.

FIG. 4 is a schematic view of the clean up bag after it has been turned inside out.

FIG. 5 is a schematic view of an alternate embodiment of the clean up bag according to the present invention.

FIG. 6 is a top cross-sectional view of the clean up bag according to an alternate embodiment of the invention.

DETAILED DESCRIPTION OF THE INVENTION

Referring to FIG. 1, the present invention consists of a clean up device 10 constructed from a bag 12 and a glove 14 for use in cleaning up and disposing of toxic, hazardous, or infectious waste (not shown).

Preferably, the glove 14 is sized and shaped to receive an adult's hand and has two thumbs 16 so that the glove may be used by either left handed or right handed individuals. However, a one-handed glove (i.e. either right or left) will also work well. In the preferred embodiment, the glove is constructed from some type of heat-sealable plastic, but those skilled in the art will recognize that other materials may be used.

The bag is generally rectangular in shape and sized to receive the glove 14. In the preferred embodiment, the bag is constructed from heat-sealable plastic, similar to that from which the glove is constructed. Preferably, the plastic is opaque so when the bag is turned inside out, the contents are not visible. Again, those skilled in the art will appreciate that alternative materials may be used.

The bag has a top 18 and a bottom 20 and two opposing sides 22 and 24. Optionally, the bag can include pleats (not shown), one on each side, extending longitudinally from the top 18 of the bag 12 to the bottom 20 of the bag 12. Such optional pleats allow the baa 12 to be easily turned inside out so that the waste is contained in the interior of the clean up device 10.

Further, the bag 12 has a gathering type cord arrangement 30, shown in FIG. 3, which may be pulled from either side to secure the contents inside of the bag.

Preferably, this gathering arrangement 30 consists of a first 32 and a second 34 draw string cord. Both draw string cords 32 and 34 are located in a sleeve 36 along the top 18 of the bag 12. The sleeve 36 is formed by folding over a small portion of the bag near the top 18 and heat sealing the folded edge thereby forming the sleeve. The draw string cords 32 and 34 are both placed in the sleeve 36 so that the first cord 32 may be drawn closed from side 22 of the bag while the second cord 34 may be drawn closed from side 24 of the bag.

As shown in FIG. 3, the bag includes a plastic bag 15 which is covered with a cut-resistant material 50 such as Kevlar™. Material 50 is preferably fastened to the plastic bag with an adhesive, and covers the entire outside surface of the plastic bag to prevent puncture of the bag by glass or needles or other sharps. Layered over material 50 is an absorbent towel 52 (attached by adhesive), which is shown covering the entire surface of material 50 but optionally need only cover selected portions of the material 50, such as the surface of material 50 on the side 38 opposite the inside surface of the bag 15 to which the glove is attached. Towel 52 is preferably a corrugated cotton fabric which is often used in hospital settings; however, it will be appreciated by those skilled in the art that any type of absorbent fabric may be used. Towel 52 absorbs any liquid surrounding or contained in the waste.

Optionally, as shown in FIGS. 5 and 6, a pad 54 is attached by adhesive or stitching to the towel 52 on side 38 of the bag. The pad 54 or other such absorbent pad is preferably gauze for medical applications, and is attached to provide additional absorbency. Preferably, pad 54 may be a 4"×4" or 4"×6" (or larger) surgical gauze positioned into the approximate center of the bag side 38 for added absorbency of open wounds or in direct surgical procedures where fluids and blood would have to be absorbed very or fairly quickly. Optionally, the gauze 54 (or towel 52) can be premedicated (substance 56, such as a medication or disinfectant), pre-sterilized, pre-sanitized, etc., and already packaged that way, ready to off-set possible infection at the clean-up site when the bag with gauze is applied. In addition, due to the increased absorbency, a disinfectant or sanitizing solution could be applied directly to the gauze insert during use and then applied to the area or open wound for infection control. The absorbent towel layer 52 or pad 54 may be impregnated or soaked or covered with a cleaning material such as a solvent, in the case of use of the bag to clean up a toxic waste. Also, the pad 54 may be adapted for special functions such as for scrubbing a surface containing a toxic, hazardous or infectious waste.

The clean up device 10 is preferably constructed by heat sealing the plastic glove 14 to one interior side 42 of the bag 12. In operation, the user places his or her hand inside the plastic glove 14 which is located on the inside 42 of the plastic bag 12. The user then grasps the inside of the bag and uses the glove to control the movement of the outside surface of the bag for cleaning, or to grasp objects such as sharps or other hazardous or infectious objects to be disposed of. The device may be used to clean up liquids, blood, mucus, sinews, bodyparts, feces and other various spilled substances required to be cleaned up in and around a hospital, nursing home, clinic, day care, home care/nursing or any medical emergency situation. The paper toweling is optionally strong enough to permit it to be moistened first and applied to the area(s) for intended clean-up, if desired. Soap, disinfectants, sterilizing solutions can be applied to the paper toweling material 52 and/or pad 54 first for easier clean up; or, it can be used in the dry format, for easy absorbency. The towel 52 and/or gauze 54 absorbs moisture and thus, helps with gripping objects and allows for spills or blood to be cleaned up. Further, the padding 40 prevents the user from feeling the texture and heat content of the waste, if such is present. Optionally, a pad 54 or the towel 52 may be of a heat resistant material to allow for the handling of hot objects or materials.

After the user has picked up or wiped up the waste, the user will use its other hand to turn the plastic bag 12 inside out (FIG. 4). When the bag 12 is turned inside out, the user can then remove his or her hand from the plastic glove 14 and grasp both ends of the draw strings 32 and 34 and tighten them so that the bag is closed. Thus, when complete, the waste is contained on the interior of the bag. The invention thus has applications in medical, industrial and household cleaning areas.

While it is contemplated that the invention is best used as a disposable product, in some cases the bag and paper toweling could be rinsed out, hung to dry, and re-used several times before the paper would give way or show signs of wear. As another alternative, the bag could have a layer of linen or cotton absorbent material instead of the paper toweling and be reused repeatedly until the plastic bag started to show signs of wear—at that time, it could be turned inside-out and permanently discarded.

Various alternated embodiments of the invention are possible, as set forth below:

1) the interior plastic bag and draw-string could be colored in red to indicate toxic waste.
2) The entire "exterior" of bag with toweling material, cut resistant fabric/material is in white or blue to indicate use in a surgical/hospital/medical environment—the interior plastic bag which becomes the exterior, enveloping closure on the interior contents when turned inside out—could be red, white, or pastel blue, or transparent, (depending on designated needs such as infectious wastes), regular safe disposal waste, etc.
3) The paper toweling material could be exchanged for "cotton," "linen," or some synthetic combination of fibers which would have a high absorbency rate or quality to the material.
4) The size of the clean-up device or bag could be expanded or enlarged for major surgical procedures where a great deal of fluids are generated due to loss of blood and irrigation procedures. The "gauze insert" could also be enlarged and thickened (comparable to the thickness of a diaper) for various types of major surgeries requiring clean up and greater absorbency procedures. The inserted gauze would be enlarged appropriately or proportionally to meet the needs of greater absorbency required in most major surgeries. (the sample size included would be appropriate for minor surgeries; plastic surgeries, etc.). Regular sizes: 10"×14;, 10"×16" and 12"×20".
5) The clean up device can be used with medicated gauze and medical emergency situations for emergency room and paramedic vehicles would or could make this a standard clean-up device in trauma packs, operating room clean up kits, etc.
6) The bag can be used without the cut-resistant material in the case of using the pad 54 for special purpose hazardous waste clean up where sharp objects were not present, such as for scrubbing a hazardous waste and capturing the waste in the bag.
7) The bag can be used as an oil clean up bag for oil spill clean-ups on a garage floor or surface. The pad 54 can be adapted to contain a solvent material to clean up the oil or the toweling can be adapted to absorb oil.
8) A tack bag: goop on the insert and the towel exterior to clean up with. This can be used to remove sediment & dust from an automobile exterior or some other finish that must be dust-free before an application of a finishing coat or sealant is applied.
9) A bag with a "silver cloth" used to polish silver and other metals to a clean, bright new finish.
10) "Treated" material bags with ammonia, soap, detergents, various cleaning products, etc., pre-treated on the towel 52 or pad 54.
11) A sponge bag may be formed with a paper-thin sponge material on outside for wiping spills off dining room tables and pick-up garbage.
12) A Scotch Brite™ bag may be formed by attaching Scotch Brite™ cleaning material on one side of bag for scouring.
13) A shoe shine bag can be formed like he type found in better hotel rooms with advertising on one side of plastic, the opposite side would be a "buffing cloth material" for shoe polishing and the interior of plastic lined bag would contain complimentary sample sized shoe polish, sewing kit, and shampoos and soaps. Of the various alternate embodiments outlined above, those that do not involve the cleaning of sharp objects would not require a cut-resistant layer in the bag design. In particular, items 7–13 would not normally require a bag construction with a cut-resistant material.

Although the invention has been described with respect to specific embodiments and configurations, those of skill in the art will recognize that many modifications may be made thereto without departing from the spirit and scope of the claims appended hereto.

What is claimed is:

1. A clean up device comprising:

a plastic bag, said bag having a top and a bottom and a first and a second side;

a layer of cut-resistant material surrounding the exterior of said plastic bag;

a layer of absorbent material attached to an exterior surface of the cut-resistant material;

a glove attached to one interior side of said bag; and a means for closing said bag, said means being located on the top of the bag.

2. A clean up device as defined in claim 1 wherein said bag is formed from heat-sealable plastic.

3. A clean up device as defined in claim 2 wherein said glove is formed from heat-sealable plastic.

4. A clean up device as defined in claim 2 further including a gauze pad attached to an exterior surface of the absorbent material.

5. A clean up device as defined in claim 4 wherein said closing means comprises two draw string cords.

*6. A clean-up device to be worn on the hand of a user to clean up a spilled material in the presence of a sharp object, said clean-up device comprising:*

*a flexible bag, said flexible bag having a generally open top and an exterior surface, said bag defining an interior recess adapted to receive the hand of the user, at least a portion of said flexible bag including a cut-resistant material capable of resisting being cut by the sharp object, said portion of said flexible bag including said cut-resistant material being positioned so as to protect the hand of the user from the sharp object;*

*an absorbent material disposed on the exterior surface of said flexible bag; and*

*a closure mechanism for closing said generally open top of said flexible bag after the hand of the user has been removed from said interior recess and said flexible bag has been inverted.*

*7. The clean-up device of claim 6 wherein the cut-resistant material is disposed between the absorbent material and the interior recess of the flexible bag so as to protect the hand of the user placed within the interior recess of the flexible bag when the user grips the sharp object contacting the absorbent material.*

*8. The clean-up device of claim 6 wherein the cut-resistant material is disposed between the absorbent material and the interior recess of the flexible bag so as to protect the hand of the user placed within the interior recess of the flexible bag when the user is wiping up the spilled material and the sharp object contacts the layer of absorbent material.*

*9. The clean up device of claim 6 wherein the absorbent material has a peripheral edge and the cut-resistant material is disposed surrounding said peripheral edge so as to protect the hand of the user placed within the interior recess of the flexible bag when the sharp object contacts the flexible bag adjacent said peripheral edge.*

*10. The clean-up device of claim 6 wherein the layer of absorbent material is disposed on a first side of the flexible bag and the cut-resistant material is disposed on a second side of the flexible bag opposing said first side, such that the hand of the user within the interior recess may grip the sharp object through the flexible bag with the cut-resistant material interposed between the hand of the user and the sharp object, but without the layer of absorbent material being interposed between the hand of the user and the sharp object.*

*11. The clean up device of claim 6 wherein the cut-resistant material surrounds the interior recess of the flexible bag, such that the user may grip the sharp object through the flexible bag, invert the flexible bag, and close the closure mechanism such that the sharp object remains within the flexible bag substantially surrounded by the cut-resistant material.*

*12. The clean up device of claim 6 wherein the cut-resistant material is a separate layer attached to the flexible bag.*

*13. The clean up device of claim 12 wherein the separate layer substantially surrounds the interior recess.*

*14. The clean up device of claim 12 wherein the separate layer is attached to the exterior surface of the flexible bag.*

*15. The clean up device of claim 6 wherein the flexible bag includes a glove member having a first thumb-receiving area and an opposing second thumb-receiving area, said glove member being attached to the flexible bag within the interior recess.*

*16. The clean up device of claim 6 wherein the closure mechanism is at least one drawstring cord generally surrounding the open top of the flexible bag.*

*17. The clean up device of claim 6 wherein the absorbent material is a separate layer attached to the exterior surface of the flexible bag.*

*18. The clean up device of claim 6 wherein the flexible bag is fabricated from a plastic material.*

* * * * *